United States Patent
Nonaka

(10) Patent No.: US 7,858,106 B2
(45) Date of Patent: Dec. 28, 2010

(54) ANTIMICROBIAL FIBER AND ITS PRODUCTION METHOD, AND ANTIMICROBIAL FIBER PRODUCT COMPRISING THE ANTIMICROBIAL FIBER, ITS PRODUCTION METHOD AND REGENERATION METHOD

(75) Inventor: Eiji Nonaka, Tokyo (JP)

(73) Assignee: Alcare Co., Ltd., Tokyo (JP)

( * ) Notice: Subject to any disclaimer, the term of this patent is extended or adjusted under 35 U.S.C. 154(b) by 98 days.

(21) Appl. No.: 11/995,769

(22) PCT Filed: Sep. 20, 2007

(86) PCT No.: PCT/JP2007/068261

§ 371 (c)(1),
(2), (4) Date: Apr. 8, 2008

(87) PCT Pub. No.: WO2008/035734

PCT Pub. Date: Mar. 27, 2008

(65) Prior Publication Data

US 2010/0113537 A1 May 6, 2010

(30) Foreign Application Priority Data

Sep. 21, 2006 (JP) .............................. 2006-255769

(51) Int. Cl.
*A01N 25/00* (2006.01)
*A61F 9/70* (2006.01)

(52) U.S. Cl. ....................... 424/405; 424/443

(58) Field of Classification Search ................. 424/405, 424/443
See application file for complete search history.

(56) References Cited

U.S. PATENT DOCUMENTS

| 4,200,735 A | 4/1980 | Sano et al. |
| 2003/0180346 A1 | 9/2003 | Woods |

FOREIGN PATENT DOCUMENTS

| JP | 5-043409 | 2/1993 |
| JP | 5-195438 | 8/1993 |
| JP | 09-059868 | 3/1997 |
| JP | 09-067750 | 3/1997 |
| JP | 09-228241 | 9/1997 |
| JP | 09-291456 | 11/1997 |
| JP | 09-328402 | 12/1997 |
| JP | 2000-017571 | 1/2000 |
| JP | 2004-509220 | 3/2004 |
| JP | 2007-169825 | 7/2007 |
| WO | WO02/22923 | 3/2002 |

OTHER PUBLICATIONS

European Search Report—EP 07 80 7625, (2007).

*Primary Examiner*—Raymond J Henley, III
(74) *Attorney, Agent, or Firm*—Young & Thompson

(57) ABSTRACT

An antimicrobial fiber bearing an anionic functional group, and a method of producing it wherein at least a part of the anionic functional group forms a quaternary ammonium salt and at least another part thereof forms an antimicrobial metal salt. The quaternary ammonium salt is preferably a cetylpyridinium salt, and the antimicrobial metal salt is preferably a zinc salt. The fiber is preferably a carboxyalkylated cellulose fiber. An antimicrobial fiber product comprising the antimicrobial fiber.

20 Claims, No Drawings

ANTIMICROBIAL FIBER AND ITS PRODUCTION METHOD, AND ANTIMICROBIAL FIBER PRODUCT COMPRISING THE ANTIMICROBIAL FIBER, ITS PRODUCTION METHOD AND REGENERATION METHOD

TECHNICAL FIELD

The present invention relates to an antimicrobial fiber having excellent antimicrobial potency, its production method, an antimicrobial fiber product comprising the antimicrobial fiber and its production method. More precisely, the invention relates to a fiber that bears an anionic functional group and a specific structure to exhibit an antimicrobial function and exhibits excellent antimicrobial potency, its production method, an antimicrobial fiber product comprising the antimicrobial fiber and its production method.

The invention also relates to a regeneration method for antimicrobial fiber products, and an antimicrobial fiber product regenerated by it.

BACKGROUND ART

In the medical field, etc., a lot of studies of antimicrobially-processed fiber products are made for preventing infection and for keeping hygienic conditions.

Patent Reference 1 discloses a sheet prepared by incorporating a carboxymethyl cellulose quaternary ammonium salt or a carboxymethyl cellulose chlorohexidine salt in wood pulp, non-wood pulp, rayon fiber, synthetic fiber, carbon fiber or the like by combined sheeting, etc. The reference says that its antimicrobial effect lasts longer than that of a sheet produced by mere antimicrobial impregnation.

On the other hand, Patent Reference 2 discloses an antimicrobial polymer composition comprising a polymer having a functional monomeric unit and an antimicrobial agent attached to the functional monomeric unit, and describes, as its example, one that comprises a quaternary ammonium salt and a cationic dye attached to an acrylic fiber.

However, it is difficult to say that the antimicrobial potency of the antimicrobial fibers described in these patent references may be sufficient.

Patent Reference 3 discloses an antimicrobial deodorizing fiber obtained by kneading a silver compound, as an antimicrobial agent, into a fiber material rich in adsorbability such as an acrylic fiber, then spinning it, and dipping the resulting fiber in a quaternary ammonium salt solution.

However, the antimicrobial deodorizing fiber is problematic in that the durability of the antimicrobial and deodorizing potency thereof is not sufficient and the effect of the antimicrobial agent in the fiber could not be fully exhibited.

Clothing such as uniforms; linens such as sheets, towels; dust control products such as mops, entrance cloths, dust mats, air conditioner filters, and others are collected and recovered, such as washed and finished, and reused, so as not to dispose of used fiber products from the viewpoint of effective utilization of natural resources, reduction in the environmental load, energy saving and the like. The regeneration and reuse are also carried out for fiber products for medical applications such as surgical clothing.

It is important that such regeneration and reuse does not provide a hygienic problem; but in a process of regeneration, the antimicrobial potency may be often lowered or lost. This may be because in the process of regeneration, the antimicrobial component may drop off from the fiber products.

Patent Reference 1: JP-A-5-43409
Patent Reference 2: JP-T-2004-509220 (WO2002/022923)
Patent Reference 3: JP-A-5-195438

DISCLOSURE OF THE INVENTION

Problems that the Invention is to Solve

Accordingly, an object of the invention is to provide an antimicrobial fiber having an excellent antimicrobial effect and exhibiting excellent durability of its antimicrobial effect, and a method for producing it.

Another object of the invention is to provide an antimicrobial fiber product comprising the antimicrobial fiber that has an excellent antimicrobial effect and exhibits excellent durability of its antimicrobial effect, and a method for producing it.

Still another object of the invention is to provide a method for regeneration of an antimicrobial fiber product for obtaining an antimicrobial fiber product that has an excellent antimicrobial effect and exhibits excellent durability of its antimicrobial effect, and an antimicrobial fiber product regenerated by it.

Means for Solving the Problems

The present inventor has assiduously studied for solving the above problems, and as a result, has found that when specific two types of structures are introduced into a fiber, then a fiber excellent in antimicrobial potency and in its durability can be obtained, and, on the basis of this finding, has completed the invention.

In that way, according to the invention, there is provided an antimicrobial fiber bearing an anionic functional group, wherein at least apart of the anionic functional group forms a quaternary ammonium salt and at least another part thereof forms an antimicrobial metal salt.

Preferably in the antimicrobial fiber of the invention, the amount of the anionic functional group that forms a quaternary ammonium salt is from 0.0006 to 0.275 mmol per gram of the fiber and the amount of the anionic functional group that forms an antimicrobial metal salt is from 0.006 to 0.275 mmol per gram of the fiber.

Also preferably in the antimicrobial fiber of the invention, the anionic functional group is a carboxy group.

Also preferably in the antimicrobial fiber of the invention, the quaternary ammonium salt is at least any one of a cetylpyridinium salt and a benzalkonium salt.

In the antimicrobial fiber of the invention, in particular, the quaternary ammonium salt is preferably a cetylpyridinium salt.

Also preferably in the antimicrobial fiber of the invention, the antimicrobial metal salt is at least any one of a zinc salt, a silver salt and a copper salt.

In the antimicrobial fiber of the invention, in particular, the antimicrobial metal salt is preferably a zinc salt.

Further in the antimicrobial fiber of the invention, in particular, the fiber bearing an anionic functional group is preferably a carboxyalkylated cellulose fiber.

Also in the antimicrobial fiber of the invention, in particular, the fiber bearing an anionic functional group is preferably a chemical fiber.

Preferably in the antimicrobial fiber of the invention, the quaternary ammonium salt is at least any one of a cetylpyridinium salt and a benzalkonium salt and the antimicrobial metal salt is at least any one of a zinc salt, a silver salt and a copper salt while the fiber is fiber bearing a carboxy group.

According to the invention, there is provided a method for producing the antimicrobial fiber of the invention, which comprises (A1) a step of contacting a fiber bearing an anionic functional group with an antimicrobial metal-containing liquid to thereby form an antimicrobial metal salt in a part of the anionic functional group, and (A2) a step of contacting the fiber with a quaternary ammonium compound-containing liquid to thereby form a quaternary ammonium salt in a part of the anionic functional group.

Also according to the invention, there is provided an antimicrobial fiber product comprising the above antimicrobial fiber of the invention.

Further, the antimicrobial fiber product of the invention is favorable for fiber products for skin contact.

Further according to the invention, there is provided a method for producing an antimicrobial fiber product, which comprises (B1) a step of contacting a fiber product containing a fiber bearing an anionic functional group with an antimicrobial metal-containing liquid to thereby form an antimicrobial metal salt in a part of the anionic functional group, and (B2) a step of contacting the fiber with a quaternary ammonium compound-containing liquid to thereby form a quaternary ammonium salt in a part of the anionic functional group.

According to the invention, there is provided a method for regenerating the antimicrobial fiber product of the invention, which comprises (C0) a step of pre-treatment of a used antimicrobial fiber product, (C1) a step of contacting the pre-treated antimicrobial fiber product with an antimicrobial metal-containing liquid to thereby form an antimicrobial metal salt in a part of the anionic functional group in the antimicrobial fiber, and (C2) a step of contacting the fiber product with a quaternary ammonium compound-containing liquid to thereby form a quaternary ammonium salt in a part of the anionic functional group.

Preferably in the method for regenerating an antimicrobial fiber product of the invention, the pre-treatment step comprises an acid treatment step and a subsequent alkali treatment step.

Further according to the invention, there is provided an antimicrobial fiber product regenerated according to the above method for regenerating an antimicrobial fiber product of the invention.

EFFECT OF THE INVENTION

The antimicrobial fiber of the invention has a broad-range antimicrobial spectrum and exhibits an excellent antimicrobial effect, and in addition, has excellent antimicrobial durability, and further, with no skin irritation, it has excellent water absorbability, feel, strength, etc.; and therefore, for preventing infections with microorganisms such as viruses, bacteria, fungi and for keeping the hygienic condition of skin, etc., it may be used in the form of yarns, fabrics (woven fabrics, knitted fabrics, or nonwoven fabrics) or fiber products produced by processing them.

The antimicrobial fiber product of the invention is useful as a fiber product for skin contact that is used in the field of medical treatments and others requiring hygienic conditions; and is favorably used as gauze, bandages, absorbent cotton, wound dressing, film dressing and adhesive plaster pads, supporters, sheets, wipers, surgical drape, surgical clothing, caps, masks, socks, stockings, etc.

Further, according to the method for regenerating antimicrobial fiber products of the invention, used antimicrobial fiber products may be regenerated in a simple manner to give antimicrobial fiber products having an excellent antimicrobial effect and excellent in the durability of the antimicrobial effect.

BEST MODE FOR CARRYING OUT THE INVENTION

The antimicrobial fiber of the invention is a fiber bearing an anionic functional group, which is characterized in that at least a part of the anionic functional group forms a quaternary ammonium salt and at least another part thereof forms an antimicrobial metal salt.

The anionic functional group that the antimicrobial fiber of the invention should bear may be any one capable of ionically dissociating to produce an anion, and its specific examples include a carboxy group, a sulfo group, a hydroxy group, etc. Of those, preferred is a carboxy group.

The anionic functional group may be one that a fiber originally bears, for example, a carboxy group of a polyamide fiber or a polyester fiber, or may also be one introduced into a fiber through a chemical reaction, for example, a carboxy group of a carboxymethylated cellulose fiber derived from a cellulose fiber.

In the antimicrobial fiber of the invention, at least a part of the anionic functional group forms a quaternary ammonium salt.

The quaternary ammoniums salt is not specifically defined; and its preferred examples include a cetylpyridinium salt, a benzalkonium salt (benzyldimethyltetradecylammonium salt, benzyldimethylhexadecylammonium salt, etc.), a benzetonium salt, a dodecyltrimethylammonium salt, etc. Of those, preferred are a cetylpyridinium salt and a benzalkonium salt; and especially preferred is a cetylpyridinium salt because it has a broad antimicrobial spectrum and hardly drops off from a fiber, and moreover exhibits an instantaneous microbicidal effect.

In the antimicrobial fiber of the invention, the amount of the anionic functional group that forms a quaternary ammonium salt is preferably from 0.0006 to 0.275 mmol per gram of the fiber, more preferably from 0.0006 to 0.183 mmol, even more preferably from 0.0006 to 0.092 mmol.

When the amount of the anionic functional group that forms a quaternary ammonium salt falls within the range, the feel of the fiber may be prevented from worsening and the fiber may exhibit an excellent antimicrobial effect with no skin irritation.

In the antimicrobial fiber of the invention, the anionic functional group forms a quaternary ammonium salt, and the quaternary ammonium salt uniformly exists in the fiber surface, and therefore, even though the amount of the quaternary ammonium salt therein is small, the fiber may exhibit a sufficient antimicrobial effect and, in addition, since the quaternary ammonium salt chemically bonds to the fiber via the anionic functional group, the fiber may have antimicrobial durability. Accordingly, the antimicrobial fiber of the invention is economically advantageous.

As compared with a case where an antimicrobial agent is kneaded in a fiber and a case where an antimicrobial agent is attached to a fiber via a binder, the invention does not detract from the characteristics such as water absorbability, feel and texture intrinsic to fibers.

In the invention, "antimicrobial agent" is a concept that includes even "an antimicrobial group" such as an antimicrobial metal and a quaternary ammonium group.

In the antimicrobial fiber of the invention, at least a part of the anionic functional group forms a quaternary ammonium salt and, in addition, at least another part of the anionic functional group forms an antimicrobial metal salt.

In the antimicrobial fiber of the invention, the amount of the anionic functional group that forms an antimicrobial metal salt is preferably from 0.006 to 0.275 mmol per gram of the fiber, more preferably from 0.0305 to 0.244 mmol.

When the amount of the anionic functional group that form an antimicrobial metal salt falls within the range, the antimicrobial fiber of the invention exhibits an excellent antimicrobial effect with no skin irritation, and may keep the texture as a skin contact material.

Not specifically defined, the antimicrobial metal may be any one capable of killing microorganisms or inhibiting their growth, for which preferred are zinc, silver, copper, etc.; and more preferred is zinc. Regarding the configuration of the antimicrobial metal salt, it may be a simple salt of an antimicrobial metal, or may be in the form of a salt of an antimicrobial metal-containing compound such as a metal complex. The antimicrobial fiber with zinc may keep its original color even after high-pressure steam sterilization, and does not discolor by oxidation or sulfidation.

Not specifically defined, the fiber that constitutes the antimicrobial fiber of the invention may be any one bearing an anionic functional group, and its examples include a carboxyalkylated cellulose fiber, a cellulose fiber graft-copolymerized with a carboxy group-bearing vinyl compound (acrylic acid, methacrylic acid, etc.), a polyamide fiber, and a fiber bearing a carboxy group such as wool (sheep wool, animal hair, etc.), silk.

The carboxy group-bearing fiber is preferably a carboxyalkylated cellulose fiber, a cellulose fiber graft-copolymerized with a carboxy group-containing vinyl compound or a polyamide fiber, and is more preferably a carboxyalkylated cellulose fiber.

The carboxyalkylated cellulose fiber may be obtained in a conventional known method, for example, by contacting a cellulose fiber with an aqueous solution containing an alkali metal hydroxide and a carboxyalkylating agent.

The cellulose fiber may be any one of natural cellulose fibers such as cotton; regenerated cellulose fibers such as viscose rayon fiber, polynosic fiber, cuprammonium rayon fiber, lyocell fiber, modal fiber; and semi-synthetic cellulose fibers such as acetate, triacetate; and may also be staple fibers or filaments.

The fiber for use in the invention is preferably chemical fibers such as regenerated fibers, semi-synthetic fibers or synthetic fibers capable of producing filaments. These fibers are hygienically favorable, because when the antimicrobial fiber of the invention is used for fiber products for skin contact such as those for medical applications and when the fiber products are cut or are used for a long period of time, the staple fibers do not drop off from the products.

In case where the antimicrobial fiber product of the invention is regenerated and repeatedly used, chemical fibers are favorable from the viewpoint of their durability, etc.

The alkali metal hydroxide for use in carboxyalkylation includes sodium hydroxide, potassium hydroxide, lithium hydroxide, rubidium hydroxide, cesium hydroxide, etc.; and sodium hydroxide is preferably used.

As the carboxyalkylating agent for use in carboxyalkylation, a halogenocarboxyic acid or its salt may be used, and preferably sodium monochloroacetate is used.

In the invention, alkali metal carboxyalkylation in the form of substitution of the hydrogen atom of a carboxy group with a metal such as an alkali metal is also within the scope of the concept of carboxyalkylation.

The carboxyalkylated cellulose fiber is preferably a carboxymethylated cellulose fiber.

The antimicrobial fiber of the invention is preferably such that the quaternary ammonium salt is at least any one of a cetylpyridinium salt and a benzalkonium salt and the antimicrobial metal salt is at least any one of a zinc salt, a silver salt and a copper salt while the fiber bears a carboxy group.

The antimicrobial fiber of the invention is more preferably such that the quaternary ammonium salt is a cetylpyridinium salt and the antimicrobial metal salt is a zinc salt while the fiber is a carboxyalkylated cellulose fiber; and an example of its structure where the fiber is a carboxymethyl cellulose fiber is shown in a formula (I).

In formula (I), n is a repetitive number of anhydrous glucose units, indicating an integer of from 50 to 10,000.

[Formula 1]

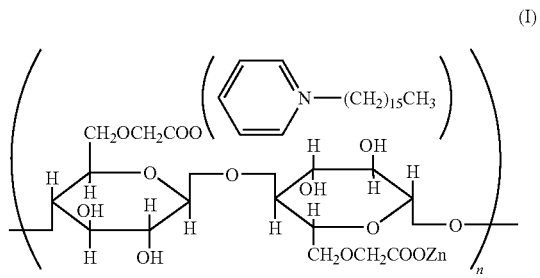

(I)

The antimicrobial fiber bearing an anionic functional group in which at least a part of the anionic functional group forms a quaternary ammonium salt and at least another part thereof forms an antimicrobial metal salt may be obtained through (A1) a step of contacting an anionic functional group-bearing fiber with an antimicrobial metal-containing liquid to thereby form an antimicrobial metal salt in a part of the anionic functional group and (A2) a step of contacting the fiber with a quaternary ammonium compound-containing liquid to thereby form a quaternary ammonium salt in a part of the anionic functional group.

In this case, regarding the order of the above step (A1) and step (A2), any one of them may be previous to the other.

As the antimicrobial metal-containing liquid for forming the antimicrobial metal salt, usable is an aqueous solution of an antimicrobial metal compound.

The antimicrobial metal compound includes salts such as sulfates, hydrochlorides, acetates, nitrates of an antimicrobial metal; hydroxides thereof; etc.

In case where the antimicrobial metal is zinc, for example, zinc sulfate, zinc chloride and zinc acetate are usable; and zinc sulfate is preferred.

In case where the antimicrobial metal is copper, for example, usable are copper sulfate, copper chloride, copper hydroxide and copper acetate; and preferred is copper sulfate.

Further, in case where the antimicrobial metal is silver, for example, usable are silver nitrate, silver sulfate, silver chloride and silver acetate; and preferred is silver nitrate.

Not specifically defined, an aqueous solution of a quaternary ammonium salt may be used as the quaternary ammonium compound-containing liquid.

The antimicrobial fiber of the invention may be used in the form of yarns or fabrics (woven fabrics, knitted fabrics, or nonwoven fabrics) or fiber products produced by processing them.

The antimicrobial fiber of the invention is favorable for antimicrobial fiber products for skin contact for use in the field of medical treatments and others that require infection prevention and hygienic conditions, for example, as gauze, bandages, wound dressing, film dressing and adhesive plaster pads, supporters, sheets, wipers, surgical drape, surgical clothing, caps, masks, socks, stockings, tights, underwear, etc.

Further, the antimicrobial fiber of the invention is useful as fiber products such as working clothes; cloths, curtains, mats, or air or liquid purification filters for animal sheds; and others for protection from influenza and other infectious diseases such as avian influenza, swine influenza, equine influenza, human influenza, or the like.

The antimicrobial fiber of the invention is effective in utilizing it for antimicrobial fiber products which, after used, are collected, then again treated for sterilization and regenerated so as to be repeatedly reusable; and are, for example, favorable for use as rental fibrous products, for example, clothing such as surgical clothing, uniforms; linens such as sheets, towels; dust control products such as mops, cloths, dust mats, filters for air purifiers, filters for air conditioners; etc.

The antimicrobial fiber product of the invention comprises the antimicrobial fiber of the invention.

The antimicrobial fiber product of the invention may be obtained by weaving, knitting or intermingling (conjugating) antimicrobial fibers of the invention to give a fiber product.

As concrete methods for weaving, knitting or intermingling (conjugating) antimicrobial fibers, any conventional known method may be employed.

The antimicrobial fiber product of the invention may also be obtained through (B1) a step of contacting a fiber product containing a fiber bearing an anionic functional group with an antimicrobial metal-containing liquid to thereby form an antimicrobial metal salt in a part of the anionic functional group, and (B2) a step of contacting the fiber product with a quaternary ammonium compound-containing liquid to thereby form a quaternary ammonium salt in a part of the anionic functional group.

In this case, regarding the order of the above step (B1) and step (B2), any one of them may be previous to the other.

The concrete processes of the step (B1) and the step (B2) may be the same as those of the step (A1) and the step (A2), respectively, in the method for producing the antimicrobial fiber of the invention.

The method for regenerating antimicrobial fiber products of the invention comprises (C0) a step of a pre-treatment of a used antimicrobial fiber product, (C1) a step of contacting the pre-treated antimicrobial fiber product with an antimicrobial metal-containing liquid to thereby form an antimicrobial metal salt in a part of the anionic functional group in the antimicrobial fiber, and (C2) a step of contacting the fiber product with a quaternary ammonium compound-containing liquid to thereby form a quaternary ammonium salt in a part of the anionic functional group.

According to the regeneration method for antimicrobial fiber products of the invention, a regenerated antimicrobial fiber product can be obtained.

The pre-treatment step is a preliminary step for efficiently attaining an antimicrobial treatment of antimicrobial fiber products to be regenerated. Concretely, it includes a step of removing the dirt from a fiber product by washing it, a step of removing the antimicrobial metal or the quaternary ammonium compound through an acid treatment, a step of an alkali treatment, a dewatering step and a drying step.

For example, in case where a fiber bearing a carboxy group that forms an antimicrobial metal salt and bearing a carboxy group that forms a quaternary ammonium salt is treated, an acid treatment with hydrochloric acid, sulfuric acid or the like results in substitution of the antimicrobial metal and the quaternary ammonium compound bonding to the carboxy group with a hydrogen atom to thereby form —COOH in the fiber. Next, an alkali treatment with sodium hydroxide or the like results in substitution of the hydrogen atom of —COOH with a sodium atom to give —COONa. The acid treatment step followed by the subsequent alkali treatment step as the pre-treatment step facilitates the subsequent sterilization treatment with an antimicrobial metal and a quaternary ammonium compound.

Next, the pre-treated antimicrobial fiber product is subjected to the step (C1) of contacting the fiber product with an antimicrobial metal-containing liquid to thereby form an antimicrobial metal salt in a part of the anionic functional group in the antimicrobial fiber, and the step (C2) of contacting the fiber product with a quaternary ammonium compound-containing liquid to thereby form a quaternary ammonium salt in a part of the anionic functional group.

The concrete processes of the step (C1) and the step (C2) may be the same as those of the step (A1) and the step (A2), respectively, in the method for producing the antimicrobial fiber of the invention.

Similarly, regarding the order of the step (C1) and the step (C2), any one of them may be previous to the other.

For grasping the amount of the quaternary ammonium salt and the antimicrobial metal salt to be bound to the antimicrobial fiber product, it is also desirable to previously determine the amount of the quaternary ammonium salt and the antimicrobial metal salt remaining in the antimicrobial fiber product to be regenerated.

If desired, a drying step for fiber products and a finishing step of ironing or the like may be added.

In case where dust control products such as mops, cloths, dust mats, filters for air purifiers and filters for air conditioners are produced as the antimicrobial fiber product, it is also desirable to further add a step of attaching an adsorbent for dust adsorption to the fibers that constitute the antimicrobial fiber product. It is desirable that the step of attaching an adsorbent is simultaneously with any one of the above step (C1) and step (C2) or after these steps.

As the adsorbent, usable is any conventional known one that contains oil, surfactant, antimicrobial, dye, etc.

As a method for attaching the adsorbent to fibers, there may be mentioned a method of contacting an adsorbent emulsion with a fiber product, etc.

In the antimicrobial fiber product of the invention, it may be anticipated that apart of the quaternary ammonium salt and the antimicrobial metal salt introduced into it as an antimicrobial site may be lost through ionic dissociation or the like during the use of the antimicrobial fiber product; but the anionic functional group bonding to the fibers that constitute the antimicrobial fiber product would hardly drop off from the fibers.

Accordingly, regeneration of the antimicrobial fiber product of the invention does not require introduction of an anionic functional group into it, and accordingly, the energy cost and the reagent cost may be remarkably suppressed, therefore making it possible to economically produce antimicrobial fiber products.

The antimicrobial fiber product of the invention may contain any other fiber than the antimicrobial fiber of the invention, as the constitutive fibers for it. Its specific examples include polyester fibers, polyolefin fibers, polyurethane fibers, polyvinyl chloride fibers, polyvinylidene chloride fibers, vinylon fibers, polyoxymethylene fibers, glass fibers, carbon fibers, etc.

Preferably, the constitutive fibers for the antimicrobial fiber product of the invention contain from 40 to 100% by weight, more preferably from 60 to 100% by weight of a cellulose fiber such as a carboxyalkylated cellulose fiber or a cellulose fiber graft-copolymerized with a carboxy group-bearing vinyl compound. The proportion of the cellulose fiber falling within the above range may make the fiber product formed of the fibers have good water absorbability and moisture absorbability and good feel.

Preferably, the antimicrobial fiber product of the invention has a water absorption of from 150 to 2,000%. Also preferably, the antimicrobial fiber product of the invention has a moisture absorption of from 4 to 20%.

The water absorption and the moisture absorption each falling within the range may make the fiber product for skin contact applications favorably absorb fluids, for example, secreted liquids or exudates, and may favorably relieve any unpleasant feel of the fiber product to skin owing to stuffiness or excessive moisture therein.

Preferably, the antimicrobial fiber product of the invention has a tensile strength of from 0.5 to 500 N/25 mm, more preferably a tensile strength of from 3 to 400 N/25 mm.

Also preferably, the antimicrobial fiber product of the invention is insoluble or indispersible in water.

The antimicrobial fiber product of the invention that is insoluble or indispersible in water and has a tensile strength falling within the above range may keep its product form with no substantial fiber structure disintegration therein, even when it is applied to skin for a long period of time and is contacted with a large amount of secreted liquids or exudates from human bodies or even when it is washed repeatedly.

Accordingly, when the product is pulled or peeled off, after the antimicrobial fiber product of the invention having the above-mentioned characteristics is used for a long period of time, for an affected part treatment or product exchange, the fibers are not cut or do not partly remain on the affected part, and may be readily removed from the affected part. Owing to such simplicity in its handling, the fiber product enables a treatment within a short period of time and may reduce the risk of infection to be caused by a complicated treatment, and, in addition, it may prevent secondary infection to be caused by the disintegrated or dropped fibers.

Preferably, the antimicrobial fiber product of the invention is white. Then, body fluid exudation and dirt adhesion may be readily recognized, and the product may have a feeling of cleanliness.

Also preferably, the antimicrobial fiber product of the invention has a color difference ($\Delta E^*ab$) in an $L^*a^*b^*$ color system of at most 20, more preferably at most 10, before and after high-pressure steam sterilization. Accordingly, even after high-pressure steam sterilization, the fiber product may not be colored so much, and therefore body fluid exudation or dirt adhesion thereon may be readily recognized, and the fiber product may have a feeling of cleanliness.

Example

The invention is described in more detail with reference to the following Examples, to which, however, the invention should not be limited. Unless otherwise specifically indicated, part and % in Examples are by mass.

Methods for evaluating the characteristics in Examples are mentioned below.

(Binding Amount of Antimicrobial Agent)

(1) In case where the antimicrobial agent is a cetylpyridinium group or a benzalkonium group:

From the bandage produced in Examples and Comparative Examples, a test piece having a dry weight of 0.5 g is collected. The test piece is dipped in 50 ml of 0.1 N hydrochloric acid, and left for 18 hours. Accordingly, the cetylpyridinium group or the benzalkonium group having bonded to the anionic functional group in the fiber is released by hydrochloric acid and converted to cetylpyridinium chloride or benzalkonium chloride.

Afterwards, the absorbance of the elute (dipping liquid) is measured with an absorptiometer (Shimadzu Seisakusho's "UV1650PC"), thereby determining the concentration (elute concentration) (mg/l) of cetylpyridinium chloride or benzalkonium chloride that is in the form of a salt as released from the fiber by hydrochloric acid.

The wavelength for determination of cetylpyridinium chloride is 260 nm, and the wavelength for determination of benzalkonium chloride is 262 nm; and calibration curves are previously formed.

Using the above numerical value of concentration, the amount of the cetylpyridinium group or the benzalkonium group having bonded to the anionic functional group in the fiber is computed according to the following formulae:

The amount, $A$(mg/g), of formed cetylpyridinium chloride or benzalkonium chloride per gram of the fiber of the test piece=[(Elute concentration (mg/l)/1,000)×50]/0.5(g).

The amount, $B$(mmol/g), of cetylpyridinium salt or benzalkonium salt per gram of the fiber of the test piece=($A$)/molecular weight of cetylpyridinium chloride or benzalkonium chloride, where the molecular weight of cetylpyridinium chloride is 358, and the molecular weight of benzalkonium chloride is 354.

(2) In case where the antimicrobial agent is an antimicrobial metal salt:

From the bandage produced in Examples and Comparative Examples, a test piece having a dry weight of 0.5 g is collected. The test piece is put into an Erlenmeyer flask equipped with a ground stopper, 50 ml of 70% sulfuric acid is added to it, and the flask is sealed up with the stopper, and for at least 10 minutes, this is shaken optionally under heat, thereby giving a solution in which the test piece has been dissolved. In the solution, the antimicrobial metal having formed a salt with the anionic functional group in the fiber has been released by sulfuric acid.

Afterwards, the absorbance of the solution is measured, using an atomic absorptiometer (Shimadzu Seisakusho's trade name "AA6700F") and a holocathode lamp (by Hamamatsu Photonics), thereby determining the concentration (elute concentration) (mg/l) of the antimicrobial metal released from the fiber by sulfuric acid.

The wavelength for determination of zinc is 213.9 nm, the wavelength for determination of copper is 324.8 nm, and the wavelength for determination of silver is 328.1 nm; and calibration curves are previously formed.

From these, the bonding amount of zinc (atomic weight 65.39), copper (atomic weight 63.55) and silver (atomic weight 107.9) having bonded to the anionic functional group in the fiber is computed according to the following formulae:

The bonding amount, $A$(mg/g), of metal per gram of the fiber of the test piece=[(Elute concentration (mg/l)/1000)×50]/0.5(g).

The bonding amount, $B$(mmol/g), of metal per gram of the fiber of the test piece=($A$)/atomic weight of metal.

(Release Ratio of Cetylpyridinium Group and Benzalkonium Group by Physiological Saline)

From the bandage produced in Examples and Comparative Examples, a test piece having a dry weight of 0.5 g is collected, and dipped in 50 ml of physiological saline (0.9% sodium chloride solution) for 1 hour.

Afterwards, the absorbance of the dipping liquid is measured with an absorptiometer (Shimadzu Seisakusho's "UV1650PC"), and the release amount (mmol/g) of the cetylpyridinium group or the benzalkonium group released from the fiber of the test piece by physiological saline is obtained according to the same method as the above method for determination of "bonding amount of antimicrobial agent".

In addition, according to the same method as the above method for determination of "bonding amount of antimicrobial agent", the bonding amount of the cetylpyridinium group or the benzalkonium group before the test piece is dipped in physiological saline is obtained as the initial bonding amount (mmol/g), and the release ratio is computed according to the following formula:

Release ratio(%)=release amount (mmol/g)/initial bonding amount (mmol/g).

(Antimicrobial Effect)

According to the method described in JIS Z 1902, a test is carried out using *Pseudomonas aeruginosa*.

From the bandage produced in Examples and Comparative Examples, 0.4 g of a test piece is cut out, 0.2 ml of a bacterial suspension is dropped onto the test piece; and immediately after the dropping, the number of the living cells is counted; and after left at 37° C. for 20 minutes, 40 minutes, 60 minutes and 240 minutes, the number of the living cells is counted. According to the following formula, the reduction in the number of the *P. aeruginosa* cells after a different period of time is computed.

After the start of the test, those with which the number of the living cells has reduced within a short period of time have an excellent instantaneous antimicrobial effect.

Cell reduction ratio(%)=[(Common logarithmic value of the number of living cells in standard fabric (non-antimicrobially-processed fabric) after left−common logarithmic value of the number of living cells in antimicrobially-processed test sample after left)/common logarithmic value of the number of living cells in standard fabric (non-antimicrobially-processed fabric) after left]×100.

(Durability of Antimicrobial Potency)

The bandage obtained in Examples and Comparative Examples is washed five times (using a washing machine, the washing condition is: rinsing two times and dewatering for 6 minutes according to the machine program, with no use of detergent). 0.4 g of a test piece is cut out from the washed bandage, 0.2 ml of a suspension of *Staphylococcus aureus* cells was dropped onto the test piece; and after left at 37° C. for 1 minute, the number of the living cells is counted. According to the following formula, the reduction in the number of the *S. aureus* cells after a different period of time is computed.

In addition, the cell reduction ratio in no washing (washing frequency, 0) is computed.

Cell reduction ratio(%)=[(Common logarithmic value of the number of living cells in standard fabric (non-antimicrobially-processed fabric) after left−common logarithmic value of the number of living cells in antimicrobially-processed test sample after left)/common logarithmic value of the number of living cells in standard fabric (non-antimicrobially-processed fabric) after left]×100.

(Tensile Strength)

Five test pieces having a width of 25 mm and a length of 200 mm are cut out from the bandage obtained in Examples and Comparative Examples, both in the machine direction and in the cross direction of the fabric. The test piece is fitted to the chuck of a tensile tester (Shimadzu Seisakusho's trade name, "Autograph AG-1", load cell 50 N) with a chuck distance of 100±1 mm, and at a pulling speed of 100 mm/min, a load is applied to it until the test piece is cut. In this stage, the maximum load is read. The test is repeated five times, and the mean value of the data is the tensile strength (N/25 mm). The tensile strength is determined both in the machine direction and in the cross direction.

The machine direction is a direction parallel to the direction in which the bandage being produced runs, that is, the longitudinal direction; and the cross direction is a direction perpendicular to the machine direction.

(Water Absorption)

A test piece of 5 cm×5 cm, as cut out of the bandage obtained in Examples and Comparative Examples, is dried at 105° C. for 2 hours, and its weight (dry weight) is measured.

Afterwards, the test piece is dipped in physiological saline (aqueous 0.9% sodium chloride solution) for 3 minutes, then taken out and hung for 1 minute to make the excess water drop off, and then its weight (weight after absorption of water) is measured.

The water absorption (%) is computed according to the following formula:

Water absorption(%)=[(weight after absorption of water−dry weight)/dry weight]×100.

(Moisture Absorption)

A test piece of 5 cm×5 cm, as cut out of the bandage obtained in Examples and Comparative Examples, is dried at 105° C. for 2 hours, and its weight (dry weight) is measured.

Afterwards, the test piece is made to absorb moisture for 12 hours in an environment at 40° C. and a humidity of 90%. After having absorbed moisture, the weight (weight after absorption of moisture) is measured, and the moisture absorption (%) is computed according to the following formula:

Moisture absorption(%)=[(weight after absorption of moisture−dry weight)/dry weight]×100.

(Color of Fiber Product)

Both test pieces before and after high-pressure steam sterilization are tested, using an autospectrophotometer (by Nippon Denshoku, using an integrating sphere NF333; test area 8 mmϕ, test distance 20 mm, viewing angle 2°), for the color difference (ΔE*ab) to be obtained according to the following color difference formula using an L*a*b* color system. In addition, the test pieces are visually checked for the color before and after high-pressure steam sterilization.

$$\Delta E^* ab = [(\Delta L^*)^2 + (\Delta a^*)^2 + (\Delta b^*)^2]^{1/2}$$

wherein ΔL* means the difference in the L* value of the test pieces before and after sterilization; Δa* means the difference in the a* value of the test pieces before and after sterilization; and Δb* means the difference in the b* value of the test pieces before and after sterilization.

Example 1

A bandage of a spun-bond nonwoven fabric formed of a continuous fiber of cuprammonium rayon was dipped in an aqueous solution of sodium monochloroacetate and sodium hydroxide dissolved therein, then dewatered to a suitable dewatering ratio, and dried to be in an absolute dry condition, thereby obtaining a bandage in which a part of the hydroxy group of the cellulose fiber was sodium carboxymethylated.

Subsequently, the bandage was dipped and neutralized in an aqueous solution of zinc sulfate heptahydrate, acetic acid and sodium acetate dissolved therein, and simultaneously the sodium carboxymethyl group was converted into a zinc-carboxymethyl group. Afterwards, the remaining zinc sulfate, acetic acid and sodium acetate were removed by washing with water, and this was dried to give a bandage in which a part of the hydroxy group of the cellulose fiber was zinc-carboxymethylated.

Next, the above zinc-carboxymethylated bandage was dipped in an aqueous cetylpyridinium chloride solution and caused to react at 60° C. for 1 hour, whereby a part of the zinc/carboxymethyl group and/or a part of the sodium carboxymethyl group still remaining with no zinc bonded thereto were converted into a cetylpyridinium-carboxymethyl group; and thereafter this was washed with water and dried. Accordingly, a bandage was obtained in which a part of the carboxy group bonding to the cellulose fiber (carboxy group of the carboxyalkylated cellulose fiber) formed a zinc salt and another part formed a cetylpyridinium salt. The bandage was evaluated for various characteristics. The results are shown in Table 1.

In Table 1, "CP" means "cetylpyridinium salt"; "BZ" means "benzalkonium salt"; and "CMated" means "carboxymethylated".

Example 2

In the same manner as in Example 1 but using a nonwoven fabric of a lyocell fiber in place of the cuprammonium rayon nonwoven fabric and using silver nitrate in place of zinc sulfate heptahydrate, obtained was a bandage in which a part of the carboxy group bonding to the cellulose fiber (carboxy group of the carboxyalkylated cellulose fiber) was silver-carboxymethylated and another part was cetylpyridinium-carboxymethylated. The bandage was evaluated for various characteristics. The results are shown in Table 1.

Example 3

In the same manner as in Example 1 but using a nonwoven fabric of a viscose rayon fiber in place of the cuprammonium rayon nonwoven fabric and using copper sulfate pentahydrate in place of zinc sulfate heptahydrate, obtained was a bandage in which a part of the carboxy group bonding to the cellulose fiber (carboxy group of the carboxyalkylated cellulose fiber) formed a copper salt and another part formed a cetylpyridinium salt. The bandage was evaluated for various characteristics. The results are shown in Table 1.

Example 4

In the same manner as in Example 1 but using benzalkonium chloride in place of cetylpyridinium chloride, obtained was a bandage in which a part of the carboxy group bonding to the cellulose fiber (carboxy group of the carboxyalkylated cellulose fiber) formed a zinc salt and another part formed a benzalkonium salt. The bandage was evaluated for various characteristics. The results are shown in Table 1.

Example 5

A bandage of a plain-knitted sheet of a polyamide fiber (nylon 66) was dipped in a solution of zinc sulfate heptahydrate and sodium hydroxide dissolved therein, for 30 minutes, whereby zinc was bonded to the carboxy group of the polyamide fiber. Afterwards, the remaining zinc sulfate and sodium hydroxide were removed by washing with water. Next, the zinc-bonded bandage was dipped in an aqueous solution of cetylpyridinium chloride dissolved therein, and reacted at 60° C. for 1 hour, whereby a part of the zinc/carboxy group and/or apart of the carboxy group still remaining with no zinc bonded thereto were converted into a cetylpyridinium-carboxy group; and thereafter this was washed with water and dried. Accordingly, a bandage was obtained in which a part of the carboxy group of the polyamide fiber formed a zinc salt and another part formed a cetylpyridinium salt. The bandage was evaluated for various characteristics. The results are shown in Table 1.

Example 6

In the same manner as in Example 1 but using a knitted fabric of cotton yarn in place of the cuprammonium rayon nonwoven fabric, obtained was a bandage in which a part of the carboxy group bonding to the cellulose fiber (carboxy group of the carboxyalkylated cellulose fiber) formed a zinc salt and another part formed a cetylpyridinium salt. The bandage was evaluated for various characteristics. The results are shown in Table 1.

Example 7

In the same manner as in Example 1 but using a knitted fabric of a cotton yarn in place of the cuprammonium rayon nonwoven fabric, obtained was a bandage in which a part of the carboxy group bonding to the cellulose fiber (carboxy group of the carboxyalkylated cellulose fiber) formed a zinc salt and another part formed a cetylpyridinium salt. The bonding amount of the antimicrobial agent per gram of the fiber of the bandage is 0.0151 mmol/g for the cetylpyridinium salt and 0.1072 mmol/g for the zinc salt.

The bandage was washed 8 times (using a washing machine, the washing condition was: rinsing two times and dewatering for 6 minutes according to the machine program, with no use of detergent); and the bonding amount of the antimicrobial agent per gram of the fiber of the bandage was measured to be found 0.0060 mmol/g for the cetylpyridinium salt and 0.0044 mmol/g for the zinc salt.

Afterwards, the bandage was treated with 1 N hydrochloric acid so as to replace zinc and cetylpyridinium bonded to the carboxy group with a hydrogen atom, whereby zinc carboxylate and cetylpyridinium carboxylate bonded to the cellulose fiber were converted into a carboxy group. Next, the bandage was treated with 0.1 N sodium hydroxide so as to replace the hydrogen atom of the carboxy group with a sodium atom, whereby the carboxy group bonded to the cellulose fiber was converted into a sodium salt.

According to the same method as above, the bandage was treated with an aqueous zinc sulfate solution and an aqueous cetylpyridinium chloride solution in that order, thereby again forming a zinc salt and a cetylpyridinium salt in the carboxy group.

Regarding the bonding amount of the antimicrobial agent per gram of the fiber of the bandage thus retreated with an antimicrobial agent, the cetylpyridinium salt was 0.0190 mmol/g and the zinc salt was 0.0791 mmol/g.

The results are shown in Table 1, in which the column of "bonding amount of antimicrobial agent (mmol/g)" indicates only the initial bonding amount before washing. Regarding the results of "antimicrobial effect (%) after 20 minutes, 40 minutes, 60 minutes and 240 minutes", the effect after 20 minutes was 90% and that of the others was 100% both for the unwashed bandage and reprocessed bandage.

Comparative Example 1

A sheet-type bandage of the same cuprammonium rayon nonwoven fabric as in Example 1 was dipped in an aqueous solution of sodium monochloroacetate and sodium hydroxide dissolved therein, then dewatered to a suitable dewatering ratio, and dried to be in an absolute dry condition; and then, the bandage was dipped and neutralized in an aqueous solution of acetic acid and sodium acetate dissolved therein, then washed with water and dried, thereby giving a bandage in which a part of the hydroxy group of the cellulose fiber was sodium carboxymethylated.

Next, the sodium carboxymethylated bandage was dipped in an aqueous benzalkonium chloride solution, and reacted at 60° C. for 1 hour, whereby the sodium carboxymethyl group was converted into a benzalkonium-carboxymethyl group; and thereafter this was washed with water and dried. Accordingly, a bandage was obtained in which a part of the carboxy group bonded to the cellulose fiber (carboxy group of the carboxyalkylated cellulose fiber) formed a benzalkonium salt. The bandage was evaluated for various characteristics. The results are shown in Table 1.

Comparative Example 2

A sheet-type bandage of the same cotton knitted fabric as in Example 6 was dipped in an aqueous cetylpyridinium chloride solution having the same concentration as in Example 1, and caused to react at 60° C. for 1 hour, whereby cetylpyridinium chloride was adsorbed by a part of the cellulose fiber. Afterwards, this was washed with water and dried, thereby giving a bandage in which a part of the cellulose fiber adsorbed cetylpyridinium salt. The bandage was evaluated for various characteristics. The results are shown in Table 1.

Comparative Example 3

In the same manner as in Example 1 but omitting the treatment with cetylpyridinium chloride, obtained was a bandage in which a part of the carboxy group bonding to the cellulose fiber (carboxy group of the carboxyalkylated cellulose fiber) formed a zinc salt. The bandage was evaluated for various characteristics. The results are shown in Table 1.

The results in Table 1 confirm the following:

The fiber, in which the anionic functional group (carboxy group) partly formed a quaternary ammonium salt but did not have an antimicrobial metal salt (Comparative Example 1), and the fiber, in which the anionic functional group (carboxy group) partly formed an antimicrobial metal salt (zinc salt) but did not have a quaternary ammonium salt (Comparative Example 3), have both poor instantaneous antimicrobial potency against *Pseudomonas aeruginosa*.

In the fiber merely dipped in an aqueous quaternary ammonium salt solution (Comparative Example 2), the antimicrobial agent did not bond to the fiber; and therefore, the instantaneous antimicrobial effect of the fiber is low, and in addition, the antimicrobial effect of the fiber after washed is also low.

On the contrary, the antimicrobial fibers of the invention in which a part of the anionic functional group (carboxy group) formed a quaternary ammonium salt and another part thereof formed an antimicrobial metal salt (Examples 1 to 6) show a synergistically high antimicrobial effect, and are excellent especially in the instantaneous antimicrobial effect (antimicrobial effect within 60 minutes), as compared with the case where the anionic functional group (carboxy group) formed a quaternary ammonium salt alone and the case where it formed an antimicrobial metal salt alone.

In addition, the antimicrobial fibers of the invention showed a good antimicrobial effect even after washed, and are excellent in the durability of the antimicrobial potency.

Further, in the case where a cetylpyridinium group is bonded to the anionic functional group of the fiber, the release ratio of the antimicrobial agent is extremely low, as compared with the case where a benzalkonium group is used (comparison between Example 1 and Example 4). Accordingly, it is considered that the antimicrobial fiber having a cetylpyridinium group could be expected to have a long-lasting antimicrobial effect even though in contact with sweat, etc.

Further, the antimicrobial fiber product of the invention may recover its excellent antimicrobial potency after a regeneration treatment (Example 7).

TABLE 1

|  | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|
| Fiber | CMated cuprammonium rayon | CMated lyocell | CMated viscose rayon | CMated cuprammonium rayon | Polyamide | CMated cotton | CMated cotton | CMated cuprammonium rayon | Cotton | CMated cuprammonium rayon |
| Bonding Amount of Antimicrobial Agent (mmol/g) | | | | | | | | | | |
| CP | 0.03 | 0.042 | 0.0351 | — | 0.0245 | 0.026 | 0.0151 | — | 0.0035 | — |
| BZ | — | — | — | 0.03 | — | — | — | 0.08 | — | — |
| Zinc | 0.05 | — | — | 0.05 | 0.11 | 0.073 | 0.1072 | — | — | 0.08 |

TABLE 1-continued

|  | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|
| Silver | — | 0.132 | — | — | — | — | — | — | — | — |
| Copper | — | — | 0.0852 | — | — | — | — | — | — | — |
| Antimicrobial Effect (%) | | | | | | | | | | |
| After 20 minutes | 65 | 100 | 100 | 90 | 100 | 89 | 90 | 16 | 3 | 2 |
| After 40 minutes | 100 | 100 | 100 | 100 | 100 | 100 | 100 | 34 | 5 | 12 |
| After 60 minutes | 100 | 100 | 100 | 100 | 100 | 100 | 100 | 78 | 4 | 30 |
| After 240 minutes | 100 | 100 | 100 | 100 | 100 | 100 | 100 | 100 | 45 | 100 |
| Antimicrobial Durability (%) | | | | | | | | | | |
| Washing 0 time | 100 | 100 | 100 | 100 | 100 | 100 | — | 100 | 100 | 4 |
| Washing 5 times | 100 | 100 | 100 | 100 | 100 | 100 | — | 100 | 51 | 5 |
| Release Ratio (%) | 3 | 3 | 3 | 53 | 5 | 5 | — | 50 | 15 | — |
| Water Absorption (%) | 1456 | 1494 | 1356 | 1421 | 919 | 424 | 402 | 1468 | 429 | 1501 |
| Moisture Absorption (%) | 11 | 6 | 9 | 10 | 2 | 10 | 10 | 10 | 9 | 10 |
| Tensile Strength (N/25 mm) | | | | | | | | | | |
| Machine direction | 16 | 11 | 7 | 15 | 50 | 279 | 250 | 16 | 285 | 16 |
| Cross direction | 12 | 7 | 6 | 11 | 47 | 70 | 62 | 12 | 68 | 12 |
| Color of Fiber Product | | | | | | | | | | |
| Color difference before and after sterilization | 1.89 | 49.62 | 15.26 | 2.68 | 3.2 | 1.82 | 1.87 | 2.01 | 1.61 | 1.28 |
| Color before sterilization | white | white | light blue | white | pale yellow | white | white | white | white | white |
| Color after sterilization | white | black | olive green | white | pale yellow | white | white | white | white | white |

The invention claimed is:

1. An antimicrobial fiber bearing an anionic functional group, wherein at least a part of the anionic functional group forms a quaternary ammonium salt and at least another part thereof forms an antimicrobial metal salt.

2. The antimicrobial fiber as claimed in claim 1, wherein the amount of the anionic functional group that forms a quaternary ammonium salt is from 0.0006 to 0.275 mmol per gram of the fiber and the amount of the anionic functional group that forms an antimicrobial metal salt is from 0.006 to 0.275 mmol per gram of the fiber.

3. The antimicrobial fiber as claimed in claim 1, wherein the anionic functional group is a carboxy group.

4. The antimicrobial fiber as claimed in claim 1, wherein the quaternary ammonium salt is at least any one of a cetylpyridinium salt and a benzalkonium salt.

5. The antimicrobial fiber as claimed in claim 4, wherein the quaternary ammonium salt is a cetylpyridinium salt.

6. The antimicrobial fiber as claimed in claim 1, wherein the antimicrobial metal salt is at least any one of a zinc salt, a silver salt and a copper salt.

7. The antimicrobial fiber as claimed in claim 6, wherein the antimicrobial metal salt is a zinc salt.

8. The antimicrobial fiber as claimed in claim 1, wherein the fiber bearing an anionic functional group is a carboxyalkylated cellulose fiber.

9. The antimicrobial fiber as claimed in claim 1, wherein the fiber bearing an anionic functional group is a chemical fiber.

10. The antimicrobial fiber as claimed in claim 1, wherein the quaternary ammonium salt is at least any one of a cetylpyridinium salt and a benzalkonium salt, the antimicrobial metal salt is at least any one of a zinc salt, a silver salt and a copper salt, and the fiber bearing an anionic functional group is a fiber bearing a carboxy group.

11. A method for producing an antimicrobial fiber of claim 1, which comprises (A1) a step of contacting a fiber bearing an anionic functional group with an antimicrobial metal-containing liquid to thereby form an antimicrobial metal salt in a part of the anionic functional group, and (A2) a step of contacting the fiber with a quaternary ammonium compound-containing liquid to thereby form a quaternary ammonium salt in a part of the anionic functional group.

12. An antimicrobial fiber product comprising an antimicrobial fiber of claim 1.

13. The antimicrobial fiber product as claimed in claim 12, which is a fiber product for skin contact.

14. A method for producing an antimicrobial fiber product of claim 12, which comprises (B1) a step of contacting a fiber product comprising a fiber bearing an anionic functional group with an antimicrobial metal-containing liquid to thereby form an antimicrobial metal salt in a part of the anionic functional group, and (B2) a step of contacting it with a quaternary ammonium compound-containing liquid to thereby form a quaternary ammonium salt in a part of the anionic functional group.

15. A method for regenerating an antimicrobial fiber product of claim 12, which comprises (C0) a step of pre-treatment of the antimicrobial fiber product after used, (C1) a step of contacting the pre-treated antimicrobial fiber product with an antimicrobial metal-containing liquid to thereby form an antimicrobial metal salt in a part of the anionic functional group in the antimicrobial fiber, and (C2) a step of contacting the fiber product with a quaternary ammonium compound-containing liquid to thereby form a quaternary ammonium salt in a part of the anionic functional group.

16. The method for regenerating an antimicrobial fiber product as claimed in claim 15, wherein the pre-treatment step comprises an acid treatment step and a subsequent alkali treatment step.

17. An antimicrobial fiber product regenerated according to a method for regenerating an antimicrobial fiber product of claim 15.

18. The antimicrobial fiber as claimed in claim 2, wherein the anionic functional group is a carboxy group.

19. A method for producing an antimicrobial fiber product of claim 13, which comprises (B1) a step of contacting a fiber product comprising a fiber bearing an anionic functional group with an antimicrobial metal-containing liquid to thereby form an antimicrobial metal salt in a part of the anionic functional group, and (B2) a step of contacting it with a quaternary ammonium compound-containing liquid to thereby form a quaternary ammonium salt in a part of the anionic functional group.

20. A method for regenerating an antimicrobial fiber product of claim 13, which comprises (C0) a step of pre-treatment of the antimicrobial fiber product after used, (C1) a step of contacting the pre-treated antimicrobial fiber product with an antimicrobial metal-containing liquid to thereby form an antimicrobial metal salt in a part of the anionic functional group in the antimicrobial fiber, and (C2) a step of contacting the fiber product with a quaternary ammonium compound-containing liquid to thereby form a quaternary ammonium salt in a part of the anionic functional group.

* * * * *